United States Patent [19]

Smith et al.

[11] Patent Number: 4,769,383
[45] Date of Patent: Sep. 6, 1988

[54] DIOXONAPHTHOTRIAZOLES HAVING ANTIALLERGIC ACTIVITY

[75] Inventors: Harry Smith, Maplehurst, Nr. Horsham; Derek R. Buckle, Redhill, both of England

[73] Assignee: Beecham Group p.l.c., England

[21] Appl. No.: 906,097

[22] Filed: Sep. 10, 1986

Related U.S. Application Data

[63] Continuation of Ser. No. 785,453, Oct. 8, 1985, abandoned, which is a continuation of Ser. No. 398,314, Jul. 15, 1982, abandoned.

[30] Foreign Application Priority Data

Aug. 6, 1981 [GB] United Kingdom ................. 8124098

[51] Int. Cl.$^4$ ..................... A61K 31/41; C07D 249/22
[52] U.S. Cl. ..................... 514/359; 548/259; 548/260; 548/261
[58] Field of Search ................ 514/359; 548/257, 259, 548/261, 256, 260

[56] References Cited

U.S. PATENT DOCUMENTS

| | | | |
|---|---|---|---|
| 4,012,407 | 3/1977 | Doyle | 549/283 |
| 4,207,335 | 6/1980 | Buckle | 549/283 |
| 4,248,879 | 2/1981 | Buckle | 548/256 |
| 4,263,309 | 4/1981 | Buckle | 548/259 |
| 4,378,360 | 3/1983 | Buckle | 548/259 |
| 4,405,620 | 9/1983 | Buckle | 548/256 |
| 4,427,686 | 1/1984 | Buckle | 548/256 |
| 4,454,136 | 6/1984 | Buckle | 548/256 |

FOREIGN PATENT DOCUMENTS

2803230 7/1978 Fed. Rep. of Germany ...... 549/283

Primary Examiner—Donald G. Daus
Assistant Examiner—Mark W. Noel
Attorney, Agent, or Firm—Jacobs & Jacobs

[57] ABSTRACT

A compound of formula (I):

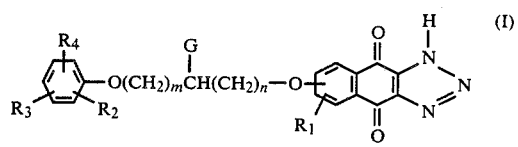

or a pharmaceutically acceptable salt thereof, wherein $R_1$ is a hydrogen atom or a $C_{1-6}$ alkyl group, $R_2$, $R_3$ and $R_4$ are the same or different and are selected from hydrogen, hydroxyl, halogen, $C_{1-4}$ alkyl, $C_{1-4}$ alkoxy and $C_{1-4}$ alkanoyl; G is a hydrogen atom or a hydroxyl group, and m and n are independently integers of from 1 to 3, with the proviso that when G is a hydroxyl grup, m or n is 1;

is useful in the treatment of asthma.

8 Claims, No Drawings

DIOXONAPHTHOTRIAZOLES HAVING ANTIALLERGIC ACTIVITY

CROSS-REFERENCE

This is a continuation of Ser. No. 785,453 filed Oct. 8, 1985 which is a continuation of Ser. No. 398,314 filed July 15, 1982, both now abandoned.

This invention relates to novel compounds, pharmaceutical compositions containing them, their formulation into pharmaceutical compositions, their use in therapy, and a process for their preparation.

It is known that some types of cells are activated by antibody-antigen combination and release substances which mediate the allergic response. It has been reported that SRS-A (the slow reacting substance of anaphylaxis), released from such cells which have been activated by antibody-antigen combinations, plays an important role in the development of allergic and asthmatic phenomena.

It is known that certain nitrocoumarins and cyanohydroxycoumarins and -indanediones protect against the release of mediators of the allergic response, such as SRS-A, and inhibit their action.

We have now discovered a class of compounds which not only inhibit the release of mediator substances but also antagonize the effects of SRS-A released after the above mentioned antibody-antigen combinations. Thus these compounds are of value in the prophylaxis and treatment of diseases whose symptoms are controlled by the mediators of the allergic response, for example asthma, hay fever, rhinitis and allergic eczema.

Accordingly, the present invention provides a compound of the formula (I), and pharmaceutically acceptable salts thereof:

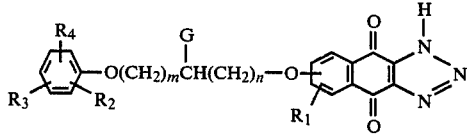

wherein
$R_1$ is hydrogen or $C_{1-6}$ alkyl;
$R_2$, $R_3$ and $R_4$ are the same or different and are chosen from hydrogen, hydroxyl, halogen, $C_{1-4}$ alkyl, $C_{1-4}$ alkoxy and $C_{1-4}$ alkanoyl;
G is H or OH; and
m and n are independently 1 to 3; with the proviso that when G is OH, one of m or n is 1.

Suitable examples of $R_1$ include hydrogen, methyl, ethyl and n- and iso-propyl. When other than hydrogen, $R_1$ is suitably in the 5-position (that is, substituting the carbon atom adjacent to the carbon atom bearing the carbonyl moiety). Preferably $R_1$ is hydrogen or 5-methyl or 5-n-propyl.

n may suitably be 1 to 2, preferably 1. More preferably m and n are each 1.

The phenoxyalkoxy side chain oxygen atom may join the naphtho[2,3-d]-v-triazole nucleus at any nonbridgehead carbon in the benzo moiety. More suitably however it will be joined at the 6-position (that is, substituting the carbon atom meta- to the carbon atom bearing the carbonyl moiety).

Examples of $R_2$, $R_3$ and $R_4$ include hydrogen, and hydroxyl.

Examples of $R_2$ to $R_4$ when halogen include fluorine, chlorine and bromine, most suitably fluorine.

Examples of suitable $C_{1-4}$ alkyl substituents falling within the definitions of $R_2$ to $R_4$ are methyl, ethyl, n- and iso-propyl, n-, iso and t-butyl, preferably n-propyl.

Examples of suitable $C_{1-4}$ alkoxy substituents falling within the definitions of $R_2$ to $R_4$ are methoxy, ethoxy, n- and iso-propoxy.

Examples of suitable $C_{1-4}$ alkanoyl groups included within the definition of $R_2$ to $R_4$ are acetyl, propionyl, and n- and iso-butyryl, preferably acetyl.

Favourably only one of $R_2$ to $R_4$ is hydroxyl. When one of these groups is hydroxyl it is favourably in the 3-position in the phenyl ring with respect to the alkylenedioxy group.

Favourably only one of $R_2$ to $R_4$ is $C_{1-4}$ alkyl. When $C_{1-4}$ alkyl, such a group is favourably in the 2-position in the phenyl ring as hereinbefore defined.

Favourably only one of $R_2$ to $R_4$ is $C_{1-4}$ alkanoyl. When $C_{1-4}$ alkanoyl, such a group is favourably in the 4-position in the phenyl ring as hereinbefore defined.

Where a highly substituted compound of formula (I) is required it will be appreciated that the substituents are to be chosen for steric compatability. For example, where two or three of the substituents are groups such as highly branched $C_{1-4}$ alkyl, $C_{1-4}$ alkoxy or $C_{1-4}$ alkanoyl groups, then these will not occupy adjacent positions.

G is preferably OH.

The triazole moiety of the compounds of formula (I) has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds.

From the aforesaid it will be appreciated that one particularly useful sub-group of compounds of the formula (I) is of formula (II):

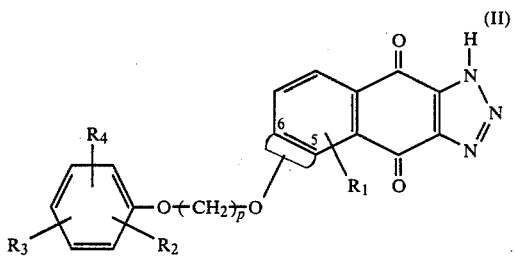

wherein p is 2 to 4; the phenoxyalkoxy side chain is joined at the 5- or 6- (as indicated) position. and the remaining variables are as defined in formula (I).

p is preferably 3.

Suitable and preferred variables $R_1$, $R_2$, $R_3$ and $R_4$ are as hereinbefore described, as are suitable and preferred substitution positions.

Thus when one of $R_2$, $R_3$ and $R_4$ is the only one of these variables to be $C_{1-4}$ alkyl it is preferably in the phenyl 2-position as hereinbefore defined. It is particularly preferably n-propyl.

When one of $R_2$, $R_3$ and $R_4$ is the only one of these variables to be hydroxy it is preferably in the phenyl 3-position as hereinbefore defined.

When one of $R_2$, $R_3$ and $R_4$ is the only one of these variables to be $C_{1-4}$ alkanoyl it is preferably in the phenyl group 4-position as hereinbefore defined.

Preferably the side chain is in the 6-position.

Preferably $R_1$, when other than hydrogen, is in the 5-position.

One preferred group of compounds of the formula (I) is of the formula (III):

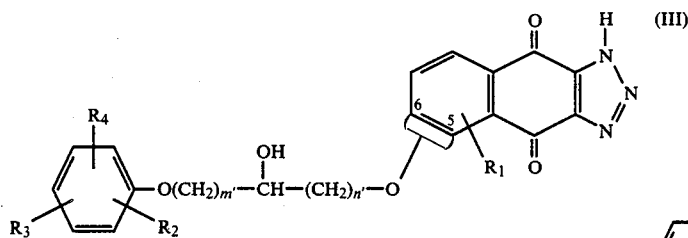

wherein
$m^1$ and $n^1$ are independently 1 or 2; the phenoxyalkoxy side chain is joined at the 5- or 6-position; and the remaining variables are as defined in formula (I).

$m^1$ and $n^1$ are preferably both 1.

Suitable and preferred variables $R_1$, $R_2$, $R_3$ and $R_4$ are as hereinbefore described under formula (II), as are suitable and preferred substitution positions.

The present invention also provides a process for the preparation of a compound of the formula (I), which process comprises the de-protection of a compound of the formula (IV):

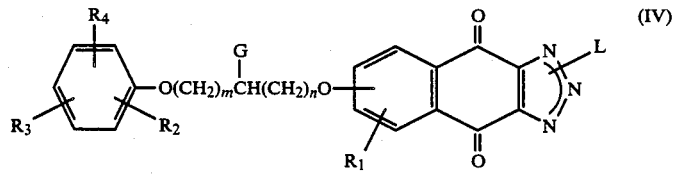

wherein L is a protecting group and the remaining variables are as defined in formula (I).

L may be any convenient protecting group removable without destruction of the rest of the molecule. Examples of suitable L groups include:

(a) Labile benzyl groups, such as 4-methoxybenzyl, which are removable for example with strong acid, such as with trifluoroacetic acid at 20°–80° C.

(b) Benzyl, or benzyl groups substituted with groups such as $C_{1-4}$ alkyl, $C_{1-4}$ alkoxy, halogen or nitro, which are removable under basic conditions with for example methoxide or ethoxide ions at slightly elevated temperatures in a solvent such as dimethyl formamide.

(c) A trityl group, or such a group in which the phenyl moieties may be substituted by one or two inert substitutents selected from $C_{1-3}$ alkyl, $C_{1-3}$ alkoxy and halogen, which groups are generally removable with mineral acid (such as hydrochloric acid) in acetic acid, again at slightly elevated temperatures.

(d) Other labile groups, such as benzhydryl.

The compounds of formula (IV) are believed to be novel, and as such form an important aspect of this invention.

The compounds of the formula (IV) may themselves be prepared by coupling a compound of the formula (V):

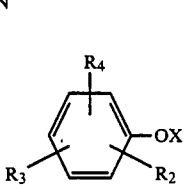

with a compound of the formula (VI):

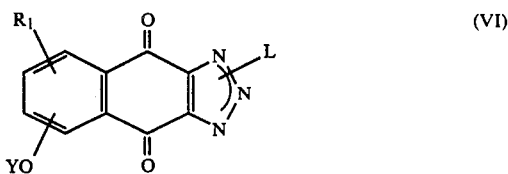

wherein

X is hydrogen and Y is a group $Z(CH_2)_mCH_2(CH_2)_n$ where Z is hydroxyl or a group readily displaceable by a nucleophile from an aliphatic moiety, or Y is hydrogen and X is a group $(CH_2)_mCH_2(CH_2)_nZ$ where Z is as defined, the remaining variables being as defined in formula (I); to give a compound of the formula (IV) wherein G is hydrogen; or wherein X is

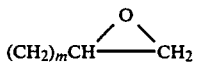

or $(CH_2)_mCH(OH)$—$CH_2Cl$ and Y is hydrogen, or Y is

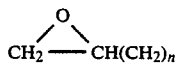

or $CH_2ClCH(OH)(CH_2)_n$ and X is hydrogen to give a compound of formula (IV) wherein G is hydroxyl and n or m respectively is 1.

When Z is a group readily displaceable by a nucleophile, suitable examples of Z include halogen atoms such as chlorine, bromine and iodine, and activated ester groups such as methanesulphonate and tosylate groups.

When one of $R_2$ to $R_4$ is hydroxyl it will in general be necessary to protect such a hydroxyl group during the above reaction. This may suitably be effected by conversion to a benzyloxy group, optionally monosubstituted by methoxy or nitro before reaction, the benzyloxy group being converted to hydroxy by conventional hydrogenolysis after the reaction. If such a hydroxy group is adjacent to another one of $R_2$ to $R_4$ which is $C_{1-4}$ alkanoyl, protection is not necessary.

When in the compounds of the formula (V) and (VI), X is a group $(CH_2)_nCH_2(CH_2)_nZ^1$ or Y is a group $Z^1(CH_2)_mCH_2(CH_2)_n$, where $Z^1$ is a group readily displaced by a nucleophile from an aliphatic moiety, when Y or X respectively are hydrogen, the reaction is generally carried out in the presence of a moderate base in a polar solvent. Examples of suitable bases include basic alkali metal salts such as the carbonates, for instance potassium carbonate. Examples of suitable solvents include ketones; such as methyl ethyl ketone.

The reaction is conveniently carried out under reflux at temperatures of 50° to 110° C. depending on the solvent, base and particular starting materials employed. The reaction time will depend on these parameters and on the temperature employed and this may readily be determined by routine trial and error. The reaction may be monitored by conventional methods such as thin layer chromatography By way of example a reaction time of up to 24 hours is often suitable.

When the compounds of the formulae (V) and (VI), X is a group $(CH_2)_mCH_2(CH_2)_nOH$ or Y is a group $HO(CH_2)_m—CH_2(CH_2)_n$, when Y and X respectively will be hydrogen, the reaction of these compounds is generally carried out in the presence of a compound of formula (VII):

$$DO_2C—N=N—CO_2E \qquad (VII)$$

wherein D and E are independently $C_{1-6}$ alkyl, aryl or aryl-$C_{1-6}$ alkyl, generally both ethyl, and a compound of formula (VIII):

$$PR_5R_6R_7 \qquad (VIII)$$

wherein $R_5$, $R_6$ and $R_7$ are independently $C_{1-6}$ alkyl, $C_{1-6}$ alkoxy, aryl, aryloxy, aryl-$C_{1-6}$ alkyl or aryl-$C_{1-6}$ alkoxy, generally all phenyl.

The reaction is generally carried out at a nonextreme temperature, such as −20° to 100° C., in an inert aprotic organic solvent such as tetrahydrofuran, dioxan, ethyl acetate or benzene.

When in the compounds of the formula (V) and (VI), X is a group

or Y is a group

when Y or X respectively will be hydrogen, the reaction is generally carried out in the presence of a phase transfer catalyst such as benzyltrimethylammonium hydroxide, conveniently at temperatures of 50° to 110° C., in a polar solvent such as dimethylformamide. A temperature dependent reaction time of 4 to 14 hours is usually sufficient.

When in the compounds of formula (V) and (VI) X is $(CH_2)_mCH(OH)CH_2Cl$ and Y is hydrogen, the reaction is conveniently carried out using the compound of formula (VI) in anion form (prepared for example with sodium hydride in dimethyl formamide), at slightly elevated temperatures of around 60°–80° C.

Compounds of the formula (V) wherein X is hydrogen are either known compounds or may be prepared analogously to known compounds.

Compounds of formula (V) wherein X is other than hydrogen may be prepared in analogous manner to the reactions described in Buckle et al, J Med Chem, 22, 158 (1979). By way of illustration, such compounds wherein X is $(CH_2)_mCH_2(CH_2)_nZ$ may be prepared by reacting the X is hydrogen compound with $B(CH_2)_mCH_2(CH_2)_nZ$ wherein B is chlorine, bromine or iodine (Z when hydroxy may be subsequently conventionally estified to give an activated ester group); and wherein X is

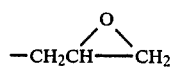

may be prepared by reacting the X is hydrogen compound with

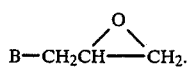

Compounds of the formula (VI) wherein Y is other than hydrogen may similarly be prepared in known manner from the corresponding Y is hydrogen compounds, for example by reacting with $Z(CH_2)_mCH_2(CH_2)_mB$ or

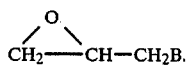

Such reactions are generally carried out in the presence of a strong base in a polar solvent, some of the polar solvent often going to form the base. Examples of suitable bases include sodium in an alcohol such as tert-butanol, sodium hydride or hydroxide in dimethylsulphoxide or dimethylformamide and lithium di-isopropylamide in hexamethylphosphoramide. Temperatures of 5° to 90° C. may be used depending on the solvent, base and particular starting materials employed. The reaction time will depend on these parameters and on the temperature employed and this may readily be determined by routine trial and error. The reaction may be monitored by conventional methods such as thin layer chromatography. By way of example a reaction time of up to 1 hour is often suitable at ambient temperatures.

Compounds of the formula (VI) wherein Y is H may be prepared by reaction of a compound of formula (X):

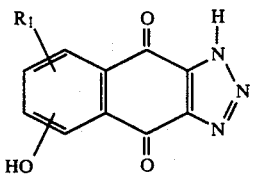

with a compound of formula LB wherein L and B are as hereinbefore defined.

The reaction may suitably be effected using a base such as alkali metal carbonate, suitably potassium, in a polar aprotic solvent such as dimethylformamide at temperatures between 20° and 120°, suitably around 40°-50° C.

It should perhaps be noted that with certain L groups, such as trityl, the N-2 protected isomer is formed preferentially which simplifies the workup procedure; but with other L groups, such as 4-methoxybenzyl, a mixture of the three possible (N-1, N-2 and N-3) protected isomers is formed, which isomers may be separated or used collectively in the coupling reactions (the end product after deprotection is the same).

Compounds of formula (X) may be prepared in a number of ways:

(a) Nitration of the naphthotriazole (XI):

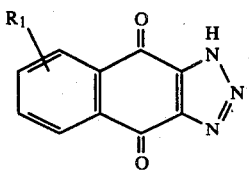

results in the formation of the 5- and 6-nitro derivatives (when $R_1$ is H, the respective ratio is 9:1) and these may be converted directly into the corresponding 5- and 6-OH compounds of formula (X) with aldoximate anion in DMSO at room temperature (having first converted the nitro derivatives to their sodium salts). The 5- and 6-derivatives may be separated either at the nitro stage, or after conversion to the hydroxy compounds, by conventional techniques.

The compounds of formula (XI) themselves may be prepared as in European Pat. No. 0 002 310.

(b) Photolysis of a naphthotriazole of formula (XI) wherein $R_1$ is hydrogen, leads directly to the 6-hydroxy derivative, the reaction being carried out in concentrated sulphuric acid at room temperature in a similar manner to that described for anthraquinone (A D Broadbent and J M Stewart, Chem Commun, 1980, 676).

(c) De-alkylation of the corresponding methyl ethers, using well known procedures such as ethylthiolate anion in N,N-dimethyl formamide (Feutrill et al, Tet Letters, 1970, 1327); lithium iodide in 2,4,6-collidine (Harrison, Chem Comm, 1969, 616); or boron trihalide-dimethylsulphide complexes (Williard et al, Tet Letters, 1980, 3731).

The methyl ethers themselves may be prepared as described in European Pat. No. 0 002 310.

As previously indicated, the compounds of formula (I) are active therapeutically.

Accordingly, this invention also provides a pharmaceutical composition comprising a compound of formula (I) as defined above, or a pharmaceutically acceptable salt thereof, and a pharmaceutically acceptable carrier.

Examples of suitable and preferred compounds for inclusion in such compositions are as previously discussed.

The compositions are of course adapted for administration to human beings.

Compounds of formula (I) which are active when given by the oral route, may be compounded in the form of syrups, tablets, capsules, pills and the like. Preferably, the compositions are in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, antioxidants or other preservatives, buffers solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

Compounds of general formula (I) may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 10 mgs via inhalation. The effective dose of compound (I) depends on the particular compound employed, the condition of the patient and on the frequency and route of administration, but in general is in the range of from 0.001 mg/kg/day to 100 mg/kg/day inclusive of the patient's body weight.

As in common practice, the composition will usually be accompanied by written or printed directions for use in the medical treatment concerned, in this case as an anti-allergic agent for the prophylaxis and treatment of for example, asthma, hay fever, rhinitis or allergic eczema.

The following Examples illustrate the preparation of compounds of this invention.

The following Descriptions illustrate the preparation of intermediates to these compounds.

DESCRIPTION 1

4,9-Dihydro-4,9-dioxo-6-hydroxy-1H-naphtho[2,3-d]-v-triazole

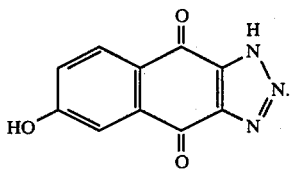

4,9-Dihydro-4,9-dioxo-1H-naphtho[2,3-d]-v-triazole monohydrate (1.8 g, 8.3 mmole) was dissolved in 98% sulphuric acid (700 ml) in a 1 liter quartz photolysis unit equipped with a medium pressure lamp. Nitrogen was passed through the apparatus and the solution was photolysed for 40 hours. The solution was poured onto ice (3 kg) and extracted with ethyl acetate. The extracts were combined, dried and evaporated to yield a yellow solid (1.3 g). HPLC and NMR showed this to be a mixture of the starting material and the title compound in approximately equal proportions. Pure hydroxy compound could be obtained by recrystallisation of a sample from chloroform and had mp 216°–7° C.

$\nu_{max}$(mull) ca 3400, 2800 (b), 1685, 1595, 1580, 1260 cm$^{-1}$.

$\delta[(CD_3)_2CO]$: 7.30 (1H, dd, J=9.0 Hz, J$_2$=2.0 Hz); 7.73 (1H, d, J=2.0 Hz); 8.17 (1H, d, J=9.0 Hz).

M+($C_{10}H_5N_3O_3$): 215.0312;

Found: C, 53.57; H, 2.44; N, 18.88; $C_{10}H_5N_3O_3.0.5$-H$_2$O requires: C, 53.58; H, 2.07; N, 18.75%.

The hydroxy compound is better separated by elution of the ammonium salts on alumina eluting first with methanol:water:0.880 ammonia (95:3:2) to remove unhydroxylated material and then with the same solvents in the ratio 70:28:2 to elute the 6-hydroxy compound as its ammonium salt. Acidification gave 0.59 g (42%; 70% on the basis of unrecovered starting material of mp (aqueous acetone) 285° C. (dec), $\nu_{max}$ (mull) 3500–2300, 1680, 1595, 1570 cm$^{-1}$.

Found: C, 51.12; H, 2.76; N, 18.00; $C_{10}H_5N_3O_2.H_2O$ requires C, 51.46; H, 3.00; N, 18.01%

DESCRIPTION 2

4,9-Dihydro-4,9-dioxo-6-hydroxy-N-(4-methoxybenzyl)naphtho[2,3-d]-v-triazole

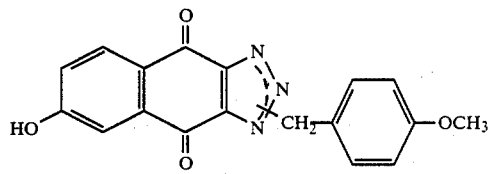

4,9-Dihydro-4,9-dioxo-6-hydroxy-1H-naphtho[2,3-d]-v-triazole (430 mg, 2.0 mmole) was treated with anhydrous potassium carbonate (152 mg, 1.1 mmole) in N,N-dimethylformamide (50 ml) and the mixture was stirred at 50° for 1 hour. 4-Methoxybenzyl chloride (500 mg, 3.2 mmole) was added and the mixture stirred at this temperature for a further 20 hours after which time the solvent was distilled in vacuo and the residue extracted with chloroform. Evaporation of the extracts gave 660 mg of a crude mixture of the three isomers of the title compound which were identified on the basis of their tlc properties. The fast running isomer being X, the second isomer being Y and the slowest running isomer being Z.

Chromatography on silica, gradient eluting with chloroform to chloroform ethanol (9:1) gave 180 mg of isomer X and 231 mg of a mixture of isomers Y and Z, giving a total yield of 411 mg (61.3%).

Isomer X: mp 267°–268° C., $\nu_{max}$(CHCl$_3$) 1695, 1660, 1652, 1630 cm$^{-1}$.

$\delta$ ((CD$_3$)$_2$CO): 3.73 (3H, s, OCH$_3$); 5.77 (2H, s, CH$_2$); 7.15 (4H, AB quartet, J 9 Hz, $\Delta\nu$ 45 Hz, aromatics); 7.25 (1H, dd, J 4.5 Hz, J$_2$ 1.5 Hz, H-7); 7.57 (1H, d, J 1.5 Hz, H$_5$); 8.10 (1H, d, J 4.5 Hz, H$_8$).

M$^+$ (C$_{18}$H$_{13}$N$_3$O$_4$): 335.0909. $\nu_{max}$ (EtOH) 229 (10,200), 249 (9,900) 397 (3,300) nm.

Isomer Y: not isolated pure.

Isomer Z: mp (isopropanol) 250° C., $\nu_{max}$ (mull) 1695, 1665, 1605, 1590, 1570, 1560, 1510 cm$^{-1}$.

$\delta$ (DMSO-d$_6$): 3.73 (3H, s); 5.92 (2H, s); 7.14 (4H, AB quartet, J 9.1 Hz, $\Delta\nu$ 32.5 Hz); 7.20 (1H, dd, J 2.5, 8.7 Hz); 7.47 (1H, d, J 2.5 Hz); 8.03 (1H, d, J 8.7 Hz); ca 11.0 (1H, broad, exchangeable).

DESCRIPTION 3

4,9-Dihydro-4,9-dioxo-5- and 6-nitro-1H-naphtho[2,3-d]-v-triazoles

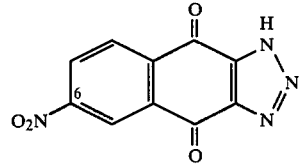

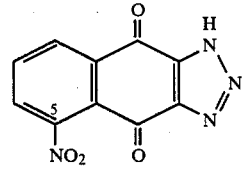

4,9-Dihydro-4,9-dioxo-1H-naphtho[2,3-d]-v-triazole (5.0 g, 25 mmole) was dissolved in sulphuric acid (30 ml) and fuming nitric acid (d=1.52, 30 ml) was added cautiously. The mixture was heated so that the internal temperature rose to 90°-100°. After 10 minutes at this temperature the mixture was poured onto ice (500 g), and the resulting precipitate filtered off, washed with water, and dried to yield a bright yellow powder (4.46 g, 74%). HPLC and NMR showed this to be a mixture of 5-nitro and 6-nitro derivatives in a ratio of ca 9:1 respectively.

Fractional recrystallisation from aqueous acetone afforded pure 5-nitro compound of mp 244°-246° C. (dec), $\nu_{max}$ (mull 3425 (br), 2600 (br), 1700, 1600, 1540, 1505 cm$^{-1}$;

$\delta[(CD_3)_2CO]$: 6.5 (3H, br, exchangeable); 8.15 (1H, d.d, J=2 Hz, 8 Hz, C-8H); 8.30 (1H, t, J=8 Hz, C-7H); 8.63 (1H, d.d, J=2 Hz, C-6H).

Found: C, 49.34; H, 1.71; N, 23.22; $C_{10}H_4N_4O_4$ requires: C, 49.19; H, 1.65; N, 22.95%.

The 6-nitro compound was isolated from the enriched mother liquors by chromatography on silica, gradient eluting with ethyl acetate-methanol, mp 253°-4° (dec) (MeOH), $\nu_{max}$ (mull) 3225 (br), 1700, 1607, 1600, 1540 cm$^{-1}$.

$\delta[(CD_3)_2CO]$: 6.5 (3H, br, exchangeable); 8.60 (1H, d, J=9 Hz); 8.85 (1H, dd, $J_1$=9, $J_2$=2 Hz); 9.00 (1H, d, J=2 Hz).

Found: C, 49.36; H, 1.57; N, 22.84. $C_{10}H_4N_4O_4$ requires C, 49.19, H, 1.65; N, 22.95%.

DESCRIPTION 4

4,9-Dihydro-4,9-dioxo-5-hydroxy-1H-naphtho[2,3-d]-v-triazole

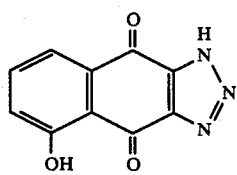

A solution of the sodium salt of 4,9-dihydro-4,9-dioxo-5-nitro-1H-naphtho[2,3-d]-v-triazole (2.70 g, 10 mmole) in dimethyl sulphoxide (DMSO, 20 ml) was added to a solution of sodium acetaldoxime [from sodium hydride (80%, 1.0 g, 33 mmole) and acetaldoxime (1.80 g, 30 mmole)] in DMSO (35 ml). The mixture was stirred for 20 hours at ambient temperature and then poured into water (500 ml). The resulting solid was filtered off, washed with water, and dried to yield (1.67 g, (76.5%) of the title compound, mp (CHCl$_3$) 235° (dec) $\nu_{max}$(KBr) 3480, 2750 (br), 1695, 1655, 1645, 1600, 1575, 1510 cm$^{-1}$.

$\delta[(CD_3)_2CO]$: 5.7 (4H, br, exchangeable); 7.33 (1H, m); 7.77 (2H, m).

$\nu_{max}$ (EtOH) nm 219 (Em=19,700); 246 (23,300); 270 (10,800); 397 (4,900).

Found: C, 55.82; H, 2.14; N, 19.33. $C_{10}H_5N_3O_3$ requires C, 55.82; H, 2.14; N, 19.53%.

Similarly the mixed 5- and 6-nitro compounds were converted to a mixture of 4,9-dihydro-4,9-dioxo-5-hydroxy-1H-naphtho[2,3-d]-v-triazole and its 6-hydroxy isomer from which the 6-hydroxy compound was isolated. This was identical to the material isolated by photolysis of 4,9-dihydro-4,9-dioxo-1H-naphtho[2,3-d]-v-triazole.

DESCRIPTION 5

4,9-Dihydro-4,9-dioxo-5-hydroxy-N-(4-methoxybenzyl)naphtho[2,3-d]-v-triazole

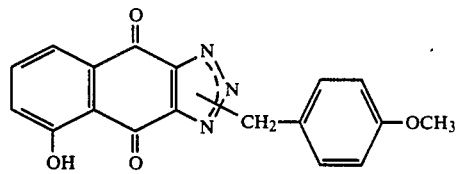

4,9-Dihydro-4,9-dioxo-5-hydroxy-1H-naphtho[2,3-d]-v-triazole (430 mg, 2 mmole) was stirred with potassium carbonate (152 mg, 1.1 mmole) and 4-methoxybenzyl chloride (329 mg, 2.10 mmole) in DMF (25 ml) at 50° for 22 hours. The DMF was evaporated in vacuo and the residue was partitioned between chloroform and dilute sodium hydroxide. Evaporation of the chloroform yielded 550 mg of a crude mixture of the three isomers of the title compound. These were identified by their tlc properties, the fastest running on silica being designated isomer A, the second being isomer B and the slowest being isomer C. Chromatography on silica eluting with chloroform-petroleum ether (4:1) gave all three isomers in reasonable purity. The total yield was 346 mg (51.6%).

Isomer A m.p. 232°

$\nu_{max}$ (CHCl$_3$) 2980 (br), 1695, 1655, 1625, 1525, 1515 cm$^{-1}$ $\delta$ (DMSO) 3.73 (3H, s); 5.85 (2H, s); 7.18 (4H, AB quartet, J 8.5 Hz, $\Delta\delta$ 45 Hz); 7.40 (1H, m); 7.75 (2H, m).

M+($C_{18}H_{13}N_3O_4$): 335.0907

Found C, 64.95; H, 3.55; N, 12.47. $C_{18}H_{13}N_3O_4$ requires: C, 64.47; H, 3.91; N, 12.53%.

$\nu_{max}$ (EtOH) 229 (Em 10,200) 249 (9,400)nm

Isomer B mp 204° (EtOH/CHCl$_3$)

$\nu_{max}$ (mull) 1695, 1650, 1610, 1545, 1515 cm$^{-1}$;

$\delta$ (CDCl$_3$) 3.84 (3H, s); 5.92 (2H, s); 7.16 (4H, AB quartet, J 9 Hz, $\Delta\nu$ 48 Hz); 7.80 (2H, m); 8.32 (1H, m), 11.86 (1H, s, exch.)

$\nu_{max}$ (MeOH) 225, 245, 276 nm.

Isomer C mp 208° (EtOH/CHCl$_3$) $\nu_{max}$(mull) 1680, 1645, 1620, 1550, 1520 cm$^{-1}$.

M+($C_{18}H_{13}N_3O_4$) 335.0929.

$\delta$ (DMSO) 3.72 (3H, s); 5.93 (2H, s); 7.14 (4H, AB quartet J 9 Hz $\Delta\nu$ 38 Hz); 7.44 (1H, s); 7.76 (2H, m), 12.10 (1H, s, exch.)

Found C; 64.43; H, 4.07; N; 12.07 $C_{18}H_{13}N_3O_4$ requires C, 64.47; H, 3.91; N; 12.53%

$\lambda_{max}$ (MeOH) 225, 247, 273 nm.

DESCRIPTION 6

6-[3-(4-Acetyl-3-hydroxy-2-n-propylphenoxy)-propoxy]-4,9-dihydro-4,9-dioxo-N-(4-methoxybenzyl)-naphtho[2,3-d]-v-triazole

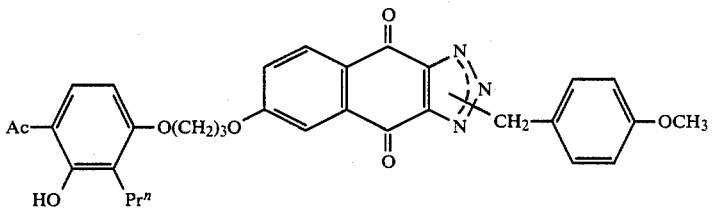

4,9-Dihydro-4,9-dioxo-6-hydroxy-N-(4-methoxybenzyl)naphtho[2,3-d]-v-traizole (Mixed isomers Y+Z) (0.402 g) was dissolved in dry tetrahydrofuran (25 ml) and triphenyl phosphine (0.480 g) and 3-(4-acetyl-3-hydroxy2-n-propylphenoxy)propan-1-ol (0.336 g) were added. The mixture was stirred at room temperature while a solution of diethyl azodicarboxylate (0.450 g) in tetrahydrofuran (5 ml) was added dropwise. After 1 hour, the solvent was evaporated and the gummy residue was triturated with ethanol to yield a buff solid (0.483 g), mp 88°–92°. Chromatography (CHCl₃) on Kieselgel 60 enabled the two isomers present to be separated.

isomer Y: Crystallised from ethanol, mp: 96°

δ (CDCl₃): 0.86 (3H, t); 1.60 (2H, q); 2.50 (7H, m, $CH_3CO+2x-CH_2-$); 3.76 (3H, s, $-OCH_3$); 4.30 (4H, dt, $2x-CH_2-$); 5.72 (2H, s, $-CH_2-Ar$); 6.44 (1H, d, J 10.0 Hz); 7.16 (4H, AB quartet $\Delta\nu$=45 Hz, J 10.0 Hz); 7.76 (3H, m); 8.24 (1H, d, J 10.0 Hz);

M⁺ ($C_{32}H_{31}N_3O_7$) 569.2194

Isomer Z: Crystallised from ethanol, mp 102°

δ (CDCl₃): 0.83 (3H, t); 1.50 (2H, q); 2.43 (7H, m, $CH_3CO+2x-CH_2-$); 3.67 (3H, s, $-OCH_3$); 4.23 (3H, dt, $2x-CH_2-$); 5.78 (2H, s, $-CH_2-Ar$); 6.43 (1H, d, J 9.0 Hz); 7.13 (4H, AB quartet $\Delta\nu$ 57 Hz, J 9.0 Hz); 7.40 (3H, m); 8.23 (1H, d, J 9.0 Hz).

M⁺ ($C_{32}H_{31}N_3O_7$) 569.2136.

EXAMPLE 1

6-[3-(4-Acetyl-3-hydroxy-2-n-propylphenoxy)propoxy]4,9-dihydro-4,9-dioxo-1H-naphtho[2,3-d]-v-triazole

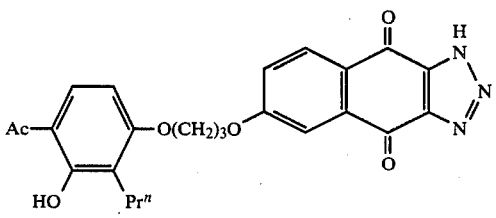

The 6-[3-(4-acetyl-3-hydroxy-2-n-propylphenoxy)-propoxy]-4,9-dihydro-4,9-dioxo-N-(4-methoxybenzyl)-naphtho[2,3-d]-v-triazole (Isomers Y and Z) obtained from the above reaction (450 mg) was stirred with trifluoroacetic acid (25 ml) at 75°–80° for 3 hours. The course of the reaction was followed by HPLC. When N-protecting starting material could no longer be detected, the reaction mixture was evaporated under reduced pressure, and the semi-solid brown residue was extracted with hot ethanol. The ethanol extract was evaporated to yield a yellow solid, which was shown to be essentially a single component by TLC/HPLC. The crude solid was chromatographed on Kieselgel 60. After fast running impurities were eluted with chloroform, the required product was eluted with chloroform-methanol (9:1) as a pale yellow solid, mp 173° C., $\nu_{max}$ (mull) 1695, 1670, 1630, 1595 cm⁻¹.

δ (CDCl₃) 0.92 (3H, t); 1.50 (2H, quintet); 2.62 (7H, m, $CH_3CO+2x-CH_2-$); 4.40 (4H, dt, $2x-CH_2-$); 6.52 (1H, d, J 10.0 Hz); 7.20–7.80 (3H, m); 8.24 (1H, d, J 10.0 Hz); 12.72 (1H, s, —OH);

M⁺ ($C_{24}H_{23}N_3O_6$) 449.1610.

(Found: C, 62.64; H, 5.02; N, 8.92; $C_{24}H_{23}N_3O_6.0.5$-H₂O requires: C, 62.87; H, 5.27; N, 9.16%)

The sodium salt was prepared by dissolution of the free triazole (210 mg) in warm ethanol, dilution with water and neutralisation with 0.47 ml of 1M aqueous sodium hydroxide. Evaporation afforded the salt which after recrystallisation from isopropanol gave 171 mg (78%) of compound mp 140° C. (dec), $\nu_{max}$ (mull) 1670, 1630, 1598 cm⁻¹;

δ (DMSO-d₆): 0.84 (3H, t, J=7 Hz, $CH_3$-CH₂); 1.44 (2H, m, $CH_2CH_3$); 2.27 (2H, t, J=7 Hz, $ArCH_2$); 2.57 (3H, s, $COCH_3$); ca 2.6 (2H, m, CH₂); 4.33 (4H, d.t, J=7 Hz, $CH_2O$); 6.70 (1H, d, J=9 Hz); 7.25 (1H, d.d, J=2.5, 9 Hz, C—7H); 7.54 (1H, d, J=2.5 Hz, C—5H); 7.81 (1H, d, J=9 Hz); 8.02 (1H, d, J=9 Hz, C—8H); 12.82 (1H, exchanged with D₂O, OH).

Found: C, 59.52; H, 5.05; N, 8.91; $C_{24}H_{22}N_3NaO_6.0.5H_2O$ requires: C, 59.99; H, 4.82; N, 8.91%.

DESCRIPTION 7

4,9-Dihydro-4,9-dioxo-6-hydroxy-2-trityl-naphtho[2,3-d]-v-triazole

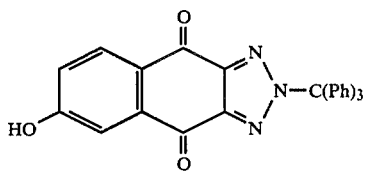

4,9-Dihydro-4,9-dioxo-6-hydroxy-1H-naphtho[2,3-d]-v-triazole monohydrate (3.45 g, 14.8 mmole) was dissolved in dry N,N-dimethylformamide (40 ml) and anhydrous potassium carbonate (1.035 g, 7.5 mmole) added. After 15 minutes at 50° C. a solution of trityl chloride (4.18 g, 15.0 mmole) in dry DMF (20 ml) was added and the mixture stirred for 20 minutes at 50° C. The solvent was removed in vacuo and the residue extracted with chloroform to give 5.16 g of crude product which on trituration with dry ether gave 4.15 g (56%) of the title compound of mp 189°–193° C. as a hemi DMF solvate.

δ (CDCl₃) 7.27 (17H, m);
7.65 (1H, d, J 3 Hz); 8.13 (1H, d, J 9 Hz);

(Found: C, 74.40; H, 4.52; N, 9.56; C29H19N3O3.0.5 (CH3)2NCHO requires: C, 74.22; H, 4.49; N, 9.93%).

DESCRIPTION 8

6-[3-(4-Acetyl-3-hydroxy-2-n-propylphenoxy)-propoxy]-4,9-dihydro-4,9-dioxo-2-trityl-naphtho[2,3-d]-v-traizole

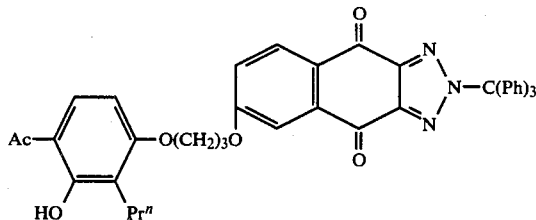

4,9-Dihydro-4,9-dioxo-6-hydroxy-2-tritylnaphtho[2,3d]-v-triazole (914 mg, 2 mmole) was dissolved in dry tetrahydrofuran (30 ml) and triphenylphosphine (580 mg, 2 mmole) and 3-(4-acetyl-3-hydroxy2-n-propylphenoxy)propan-1-ol (550 mg, 2.2 mmole) were added. After stirring at ambient temperature for a few minutes a solution of diethyl azodicarboxylate (520 mg, 3.0 mmole) in tetrahydrofuran (5 ml) was added dropwise to give a red solution which gradually changed to yellow. After 15 minutes the solvent was removed in vacuo and the residue dissolved in chloroform and chromatographed on silica to give a foam which crystallised on trituration with ethanol to give 0.833 g (59%) of the title compound of mp 103° C. as a hemihydrate.

$\nu_{max}$ (mull) 1690, 1630, 1595 cm$^{-1}$;

$\delta$ (CDCl3) 0.88 (3H, distorted t); 1.43 (2H, m); 2.30 (2H, t); 2.51 (3H, s); 2.58 (2H, t, J 6 Hz); 4.21 (2H, t, J 6 Hz); 4.32 (2H, t, J 6 Hz); 6.42 (1H, d, J 9 Hz); 7.23 (16H, m); 7.55 (1H, m); 7.71 (1H, d, J 1.5 Hz); 8.22 (1H, d, J 6 Hz); 12.7 (1H, s).

(Found: C, 73.46; H, 5.24; N, 6.07; C43H37N3O6.0.5-H2O requires: C, 73.69; H, 5.46; N, 5.99%).

EXAMPLE 2

6-[3-(4-Acetyl-3-hydroxy-2-n-propylphenoxy)-propoxy]4,9-dihydro-4,9-dioxo-1H-naphtho[2,3-d]-v-triazole

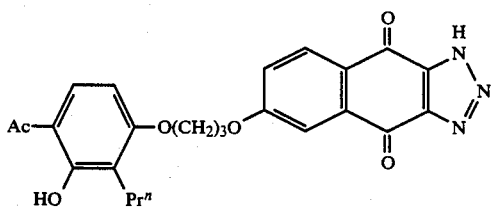

Concentrated hydrochloric acid (1 ml) was added to a solution of 6-[3-(4-acetyl-3-hydroxy-2-n-propylphenoxy)-propoxy]-4,9-dihydro-4,9-dioxo-2-tritylnaphtho[2,3-d]-v-triazole (700 mg) in glacial acetic acid (15 ml) and the mixture warmed to 40° C. for 5 minutes to effect removal of the trityl group. The solution was evaporated in vacuo and the residue triturated with methylene dichloride to give 0.298 g (66%) of the title compound of mp 173° C., identical spectroscopically with that prepared in Example 1.

DESCRIPTION 9

4,9-Dihydro-4,9-dioxo-5-hydroxy-2-trityl-naphtho[2,3-d]-v-triazole

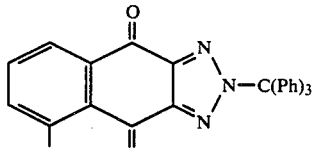

4,9-Dihydro-4,9-dioxo-5-hydroxy-1H-naphtho[2,3-d]-v-triazole (1.87 g, 8.7 mmole) and anhydrous potassium carbonate (0.60 g, 4.35 mmole) in dry N,N-dimethylformamide (25 ml) were stirred at 50° C. for 30 minutes and a solution of trityl chloride (2.42 g, 8.7 mmole) in dry DMF (10 ml) was added. The resulting mixture was stirred for 30 minutes at 50° C. and the solvent removed in vacuo. The residue was exhaustively extracted with chloroform and the extracts evaporated to give 3.82 g of yellow solid which on recrystallisation from acetone afforded 2.75 g (69%) of material of mp 135°-138° C. as an acetonate.

$\nu_{max}$ (mull) 1705, 1690, 1650, 1595, 1575, 1490 cm$^{-1}$;

$\delta$ (CDCl3) 2.15 (6H, s, acetone); 7.21 (16H, complex m); 7.61 (1H, t, J 7.5 Hz); 7.80 (1H, d, d, J 1.5, 7.5 Hz); 12.3 (1H, sharp s).

(Found: C, 74.91; H, 4.98; N, 18.19; C29H19N3O3.C3H6O requires: C, 74.55; H, 4.89; N, 8.15%),

DESCRIPTION 10

5-[3-(4-Acetyl-3-hydroxy-2-n-propylphenoxy)-propoxy]4,9-dihydro-4,9-dioxo-2-trityl-naphtho[2,3-d]-v-triazole

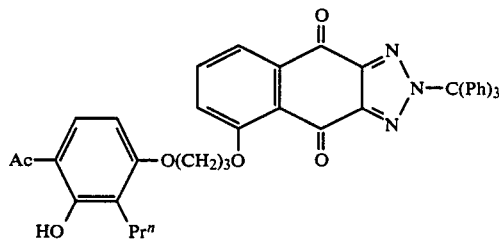

4,9-Dihydro-4,9-dioxo-5-hydroxy-2-trityl-naphtho[2,3-d]-v-triazole (1.03 1 g, 2 mmole of acetonate), triphenylphosphine (0.580 g, 2.2 mmole) and 3-(4-acetyl-3-hydroxy-2-n-propylphenoxy)propan-1-ol (0.550 g, 2.2 mmole) were dissolved in dry tetrahydrofuran (30 ml) and stirred at room temperature. A solution of diethyl azodicarboxylate (0.420 g, 2.4 mmole) in dry THF (2 ml) was added to give a red solution which gradually turned yellow. After 20 minutes the solvent was removed in vacuo and ethanol was added to the residue to give a yellow solid, 0.510 g, mp 83° C. Recrystallisation from ethanol gave 0.35 g (35%) of material mp 106°-107° C.

$\nu_{max}$ (mull) 1690, 1675, 1620, 1580, 1490 cm$^{-1}$;

$\delta$ (CDCl3) 0.88 (3H, t, J 6.8 Hz); 1.42 (2H, m); 2.39 (2H, t, J 5.3 Hz); 2.53 (3H, s); 2.61 (2H, t, J 6.7 Hz); 4.34 (2H, t, J 5.3 Hz); 4.45 (2H, t, J 5.3 Hz); 6.51 (1H, d, J 8.5 Hz); 7.24 (16H, complex m); 7.51 (1H, d, J 9 Hz); 7.75 (1H, d, J 8.2 Hz); 7.98 (1H, d.d, J 1.5, 7.5 Hz); 11.28 (1H, sharp s).

(Found: C, 74.64; H, 5.15; N, 6.07; C$_{43}$H$_{37}$N$_3$O$_6$ requires: C, 74.65; H, 5.39; N, 6.07%).

EXAMPLE 3

5-[3-(4-Acetyl-3-hydroxy-2-n-propylphenoxy)-propoxy]4,9-dihydro-4,9-dioxo-1H-naphtho[2,3-d]-v-triazole

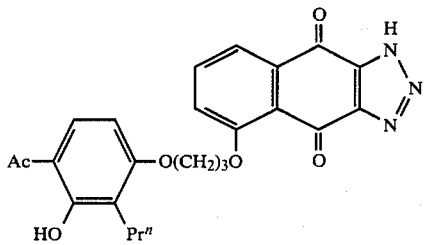

Concentrated hydrochloric acid (0.5 ml) was added to a solution of 5-[3-(4-acetyl-3-hydroxy-2-n-propylphenoxy)-propoxy]-4,9-dihydro-4,9-dioxo-2-tritylnaphtho[2,3-d]-v-triazole (0.35 g) in glacial acetic acid (10 ml) and the mixture was heated to 40° C. for 30 minutes to effect removal of the trityl group. The solution was evaporated in vacuo and the residue chromatographed on silica eluting with chloroform and then 5% methanol in chloroform to give 0.113 g (50%) of title compound of mp 183° C.

$\nu_{max}$ (mull) 1680, 1620, 1595, 1580 cm$^{-1}$.

δ (CDCl$_3$-DMSO-d$_6$) 0.87 (3H, t, J 7.2 Hz); 1.41 (2H, quintet, J 7 Hz); 2.42 (2H, t, J 7.5 Hz); 2.54 (3H, s); 2.59 (2H, t, J 6.9 Hz); 4.39 (2H, t, J 6.2 Hz); 4.47 (2H, t, J 6.2 Hz); 6.59 (1H, d, J 8.6 Hz); 7.41 (1H, d.d, J 1.2, 8.0 Hz); 7.60 (1H, d, J 8.7 Hz); 7.73 (1H, t, J 7.8 Hz); 7.89 (1H, d.d, J 1.2, 6.4 Hz); 12.70 (1H, sharp s).

M$^+$ (C$_{24}$H$_{23}$N$_3$O$_6$) 449.1591

(Found: C, 63.99; H, 5.18; N, 9.58; C$_{24}$H$_{23}$N$_3$O$_6$ requires: C, 64.13; H, 5.16; N, 9.35%).

DESCRIPTION 11

6-[3-(4-Acetyl-3-hydroxy-2-n-propylphenoxy)-2-hydroxypropoxy]-4,9-dihydro-4,9-dioxo-N-(4-methoxybenzyl)naphtho[2,3-d]-v-triazole

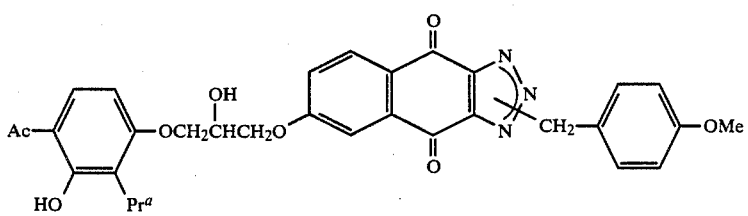

6-Hydroxy-4,9-dihydro-4,9-dioxo-N-(4-methoxybenzyl)naphtho[2,3-d]-v-triazole (585 mg, 1.74 m mole) was dissolved in dry N,N-dimethylformamide (25 ml) and 4-(2,3-epoxypropoxy)-2-hydroxy-3-n-propylacetophenone (523 mg, 1.2 equiv.) was added. To the mixture was added Triton B (15 drops) and the total stirred at 140° C. for 6 hours. The cooled mixture was evaporated under reduced pressure and water added. After adjusting the pH to 3 with dilute hydrochloric acid the product was extracted into ethyl acetate. Evaporation of the dried (MgSO$_4$) extracts and chromatography of the residue on SiO$_2$ eluting with chloroform gave the title compound 140 mg (14%) as an oil.

δ (CDCl$_3$): 1.03 (3H, t, J 7 Hz, CH$_2$—C$\underline{H}_3$); 1.52 (2H, m, C$\underline{H}_2$—CH$_3$); 2.56 (3H, s, C$\underline{H}_3$—CO); 2.64 (2H, m, C$\underline{H_2}$CH$_2$CH$_3$); 3.78 (3H, s, OC$\underline{H}_3$); 4.31 (5H, m, OC$\underline{H}_2$+OC$\underline{H}$); 5.71 (2H, s, N-C$\underline{H}_2$); 6.46 (1H, d, J 9 Hz); 7.16 (4H, $\overline{ABq}$, J 9 Hz, Δ$\nu$ 46 1 Hz, PhOMe); 7.42 (2H, m); 7.77 (1H, d, J 2.5 Hz, C-5H); 8.26 (1H, d, J 9 Hz, C-8H); 12.71 (1H, s, OH);

M$^+$ (C$_{32}$H$_{31}$N$_3$O$_8$) 585.2108.

EXAMPLE 4

6-[3-(4-Acetyl-3-hydroxy-2-n-propylphenoxy)2-hydroxypropoxy]-4,9-dihydro-4,9-dioxo-1H-naphtho[2,3-d]-v-triazole

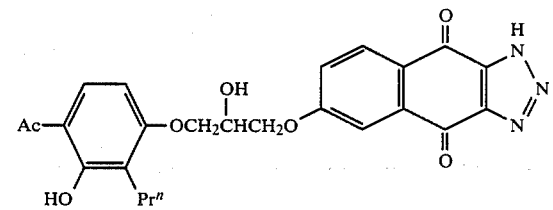

A solution of 6-[3-(4-acetyl-3-hydroxy-2-n-propylphenoxy)-2-hydroxypropoxy]-4,9-dihydro-4,9-dioxo-N-(4-methoxybenzyl)naphtho[2,3-d]-v-triazole (266 mg) in trifluoroacetic acid (15 ml) was stirred at 70° C. for 5½ hours and evaporated to dryness. The residue was slurried with water and basified to a constant pH 9.5 with dilute sodium hydroxide. The filtered solution was reacidified to pH 5.5 with acetic acid and extracted with ethyl acetate. The dried extracts (MgSO$_4$) were evaporated to a red oil. Chromatography on SiO$_2$ eluting with dichloromethane then 5% ethanol in chloroform gave 0.40 g (61%) of title compound of mp 150°-154° C.

$\nu_{max}$ 3300 (br), 1680, 1620, 1590 cm$^{-1}$.

δ (DMSO-d$_6$) 0.82 (3H, t, J 8 Hz); 1.43 (2H, m); ca 2.5 (2H, m); 2.57 (3H, s); 4.25 (5H, m); 5.5 (1H, broad exchangeable); 6.69 (1H, d, J 9 Hz); 7.35 (1H, d.d, J 9 Hz, 2.5 Hz); 7.59 (1H, d, J 2.5 Hz); 7.81 (1H, d, J 9 Hz); 8.07 (1H, d, J 9 Hz); 12.80 (1H, s, exchangeable).

EXAMPLE 5

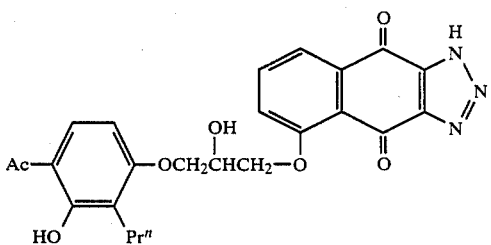

In a similar manner to Example 4, 5-[3-(4-acetyl-3-hydroxy-2-n-propylphenoxy)-2-hydroxypropoxy]4,9-dihydro-4,9-dioxo-1H-naphtho[2,3-d]-v-triazole is prepared.

PHARMACOLOGICAL DATA SECTION

Activities in biological test systems

The compounds were tested for their ability to:
(a) inhibit rat passive peritoneal anaphylaxis; and
(b) antagonise the spasmogenic effects of slow reacting substance of anaphylaxis, SRS-A, on isolated guinea pig ileum.

The methods used are described below.

Animals

Charles River Sprague Dawley male rats of 250–300 g. and Dunkin Hartley male white guinea pigs of 250–300 g. were used.

Rat Passive Peritoneal Anaphylaxis (PPA)

The method has been described previously. (Ross, Janet W., Smith, H. and Spicer, Barbara A. Increased vascular permeability during passive peritoneal anaphylaxis in the rat. Int. Arch. Allergy appl. Immun., 51, 226, 1976).

Antiserum

Rats were sensitised by giving an intraperitoneal injection of 0.5 ml of Bordetella pertussis vaccine ($4 \times 10^{10}$ organisms/ml Burroughs Wellcome, London) and a subcutaneous injection of 0.5 ml of an emulsion of 100 mg of ovalbumin (chicken egg albumin, crystallised and lyophilised, grade 3, Sigma, London) in 2 ml of isotonic saline and 3 ml of Freud's incomplete adjuvant (Difco Laboratories, Michigan, USA).

The rats were bled by cardiac puncture, on day 18, the blood was pooled, and the serum separated, stored at $-20°$ C. and thawed only before use. The serum was shown to contain immunoglobulin E (IgE) antibody by its ability to sensitise rats for passive cutaneous anaphylaxis (carried out as described: Spicer, Barbara A; Ross, Janet W., and Smith, H; Inhibition of immediate hypersensitivity reactions in the rat by disodium cromoglycate and a nitroindanedione, Clin. exp., Immunol., 21, 419 1975) to a dilution of 1:32 to 1:64 persisting for at least 72 hours after sensitisation.

Passive peritoneal anaphylaxis

Rats were each given an intraperitoneal injection of 2 ml of a 1:5 dilution of the rat anti-serum in isotonic saline. Two hours later 0.3 ml of a 5% solution of Pontamine Sky Blue (Raymond A. Lamb, London) in isotonic saline was injected intravenously, followed by an intraperitoneal injection of the test compound in 1 ml of saline; (control rats received 1 ml of saline); followed 30 seconds later by an intraperitoneal injection of 5 ml of Tyrode's solution containing 50 µg/ml heparin and 0.4 mg/ml of ovalbumin. The concentrations of the compounds were quoted as those in the 6 ml of fluid injected intraperitoneally. Exactly five minutes after challenge the rats were stunned and bled and their peritoneal fluids were collected by opening their peritoneal cavities over funnels into polycarbonate tubes in ice. The supernatants were separated from the cellular residue by centrifuging at 150 g. for five minutes and were retained for assay of dye and histamine. Any samples obviously contaminated with blood were not used for estimation of dye. Groups of at least five rats were used for each dose of compound and the treatments were randomised.

Assay of peritoneal fluids

Dye was assayed within two hours by measurement of optical density (OD) at 625 nm.

For histamine assay 0.5 ml samples of the supernatants were added to 1 ml volumes of 12% trichloracetic acid and stored at $-20°$ C. The deproteinised samples were assayed using an automated spectrofluorimetric system (Technicon Autoanalyser) by a method similar to that of Evans, D. P., Lewis, J. A. and Thomson, D. S.: (An automated fluorimetric assay for the rapid determination of histamine in biological fluids. Life Sci. 12, 327, 1973). At the concentrations used the compounds tested did not interfere with the assay.

SRS-A Antagonist Activity

The compounds have been evaluated as direct antagonists of slow reacting substance of anaphylaxis (SRS-A) by assay using the isolated guinea pig ileum.

SRS-A rat was obtained from the peritoneal cavity of the rat after passive peritoneal anaphylaxis by a method based on that of R. P. Orange, D. J. Stechschulte and K. F. Austen, J. Immunology, 105, 1087 (1970) as described by J. W. Ross, H. Smith and B. A. Spicer 1976, Increased vascular permeability during passive peritoneal anaphylaxis in the rat. Int. Arch. Allergy appl. 51, 226. The sensitising serum containing antibody was produced in rats as described by J. W. Ross et. al., ibid.

2 ml of a 1 in 5 dilution of the sensitising serum was injected by the peritoneal route into recipient rats and after 2 hours 5 ml of Tyrode's solution containing 0.4 mg/ml ovalbumin (Sigma Grade III) and 50 µg/ml heparin was injected by the same route. Five minutes after challenge the rats were stunned and bled and the peritoneal fluids collected into polycarbonate tubes in ice. After centrifugation at 150 g. for five minutes the supernatants were combined, heated in a boiling water bath for five minutes, cooled and stored at $-20°$ C. The combined peritoneal fluids contained SRS-A and were used in the antagonism studies.

The SRS-A arrays were carried out on isolated strips of guinea pig ileum in Tyrode's solution containing atropine $5 \times 10^{-7}$M and mepyramine $10^{-6}$M as described by W. E. Brocklehurst, J. Physiology, 151, 416 (1960).

The activity of the antagonists was determined by their ability to reduce submaximal responses induced by SRS-A. The antagonists were added to the 4 ml bath in 0.1 ml volumes in aqueous solution half a minute before the addition of SRS-A and were present during induced contraction.

Results

The results obtained in these tests, which are shown in the following Tables demonstrate the ability of the compounds not only to inhibit the release of mediator substances but also to antagonise the effects of released SRS-A.

| | ACTIVITIES OF COMPOUNDS IN RAT PPA | | |
|---|---|---|---|
| | | Concentration in peritoneal fluid as % of mean of controls (Mean ± SEM, 5–7 rats per group) | |
| Example | Conc$^n$ · injected i.p. (M) | Histamine | Dye |
| 1 and 2 | $2 \times 10^{-5}$ | 10 ± 1 | 32 ± 5 |
| | $2 \times 10^{-6}$ | 27 ± 8 | 58 ± 8 |

-continued

ACTIVITIES OF COMPOUNDS IN RAT PPA

| | | Concentration in peritoneal fluid as % of mean of controls (Mean ± SEM, 5-7 rats per group) | |
|---|---|---|---|
| Example | Conc$^n$ · injected i.p. (M) | Histamine | Dye |
| | $2 \times 10^{-7}$ | 57 ± 11 | 63 ± 5 |
| 3 | $2 \times 10^{-5}$ | 25 ± 3 | 57 ± 4 |
| | $2 \times 10^{-6}$ | 62 ± 11 | 94 ± 8 |
| 4 | $2 \times 10^{-7}$ | 38 ± 4 | 58 ± 4 |
| | $2 \times 10^{-8}$ | 64 ± 11 | 72 ± 11 |

Results

SRS-A Antagonism on Guinea Pig Ileum

| Example | Approximate concentration to give a 50% inhibition of a less than maximal response to SRS-A. |
|---|---|
| 1 and 2 | $4 \times 10^{-7}$ M |
| 3 | $10^{-6}$ to $10^{-5}$ M |
| 4 | $10^{-7}$ to $2.5 \times 10^{-7}$ M |

Toxicity

No toxic effects were observed in these tests.

We claim:

1. A compound selected from the group consisting of
6-[3-(4-acetyl-3-hydroxy-2-n-propylphenoxy)propoxy]-4,9-dihydro-4,9-dioxo-1H-naphtho[2,3-d]-v-triazole;
5-[3-(4-acetyl-3-hydroxy-2-n-propylphenoxy)propoxy]-4,9-dihydro-4,9-dioxo-1H-naphtho[2,3-d]-v-triazole;
6-[3-(4-acetyl-3-hydroxy-2-n-propylphenoxy)-2-hydroxy-propoxy]-4,9-dihydro-4,9-dioxo-1H-naphtho[2,3-d]-v-triazole; and
5-[3-(4-acetyl-3-hydroxy-2-n-propylphenoxy)-2-hydroxy-propoxy]-4,9-dihydro-4,9-dioxo-1H-naphtho[2,3-d]-v-triazole or a pharmaceutically acceptable salt thereof.

2. The compound according to claim 1, which is 6-[3-(4-acetyl-3-hydroxy-2-n-propylphenoxy)propoxy]-4,9-dihydro-4,9-dioxo-1H-naphtho[2,3-d]-v-triazole or a pharmaceutically acceptable salt thereof.

3. The compound according to claim 1, which is 5-[3-(4-acetyl-3-hydroxy-2-n-propylphenoxy)propoxy]-4,9-dihydro-4,9-dioxo-1H-naphtho[2,3-d]-v-triazole or a pharmaceutically acceptable salt thereof.

4. The compound according to claim 1, which is 6-[3-(4-acetyl-3-hydroxy-2-n-propylphenoxy)-2-hydroxy-propoxy]-4,9-dihydro-4,9-dioxo-1H-naphtho[2,3-d]-v-triazole or a pharmaceutically acceptable salt thereof.

5. The compound according to claim 1, which is 5-[3-(4-acetyl-3-hydroxy-2-n-propylphenoxy)-2-hydroxy-propoxy]-4,9-dihydro-4,9-dioxo-1H-naphtho[2,3-d]-v-triazole or a pharmaceutically acceptable salt thereof.

6. A pharmaceutical composition for the prophylaxis and treatment of diseases whose symptoms are controlled by the mediators of the allergic response comprising a compound according to claim 1, in combination with a pharmaceutically acceptable carrier.

7. A method of treating humans for diseases whose symptoms are controlled by the mediators of the allergic response, which comprises administering to a human an effective, non-toxic amount of a compound according to claim 1.

8. A method of treating humans for diseases whose symptoms are controlled by the mediators of the allergic response, which comprises administering to a human an effective, non-toxic amount of a composition according to claim 6.

* * * * *